United States Patent [19]

Senatore

[11] Patent Number: 5,067,795
[45] Date of Patent: Nov. 26, 1991

[54] ADJUSTABLE TRANSPARENCY SPECTACLES

[75] Inventor: Daniele Senatore, Rome, Italy

[73] Assignee: Gianni Bulgari S.p.A., Rome, Italy

[21] Appl. No.: 305,988

[22] PCT Filed: Mar. 23, 1987

[86] PCT No.: PCT/IT87/00024
§ 371 Date: Sep. 14, 1988
§ 102(e) Date: Sep. 14, 1988

[87] PCT Pub. No.: WO87/06018
PCT Pub. Date: Oct. 8, 1987

[30] Foreign Application Priority Data

Mar. 24, 1986 [IT] Italy ............... 47809 A/86

[51] Int. Cl.$^5$ .................. G02F 1/13; G02C 00/00
[52] U.S. Cl. ..................... 359/84; 351/41; 359/99; 359/90; 359/93
[58] Field of Search ............ 350/331 R, 347 R, 349, 350/340, 341, 332, 347 V, 347 E, 350 R; 351/41

[56] References Cited

U.S. PATENT DOCUMENTS

| | | | |
|---|---|---|---|
| 4,150,878 | 4/1981 | Barzilai et al. | 350/344 |
| 4,272,162 | 6/1981 | Togashi et al. | 350/347 R |
| 4,300,818 | 11/1981 | Schacher | 350/331 R |
| 4,756,605 | 7/1988 | Okada et al. | 350/347 R |
| 4,781,440 | 11/1988 | Toda | 350/347 R |

FOREIGN PATENT DOCUMENTS

| | | | |
|---|---|---|---|
| 0046227 | 3/1982 | Japan | 350/347 R |
| 0220221 | 9/1988 | Japan | 350/347 R |
| 0274923 | 11/1988 | Japan | 350/347 R |
| 0639001 | 10/1983 | Switzerland | . |

OTHER PUBLICATIONS

White et al., "New Absorptive Mode Reflective Liquid Crystal Display Device", Journal of Applied Physics, vol. 45, No. 11, Nov. 1974, pp. 4718–4723.

Gharadjedaghi et al., "Mathematical Simulation of a Positive Contrast Guest–Host Display Using Nematic crolesteric Phase Change", J. Appl. Phys. 53(11), Nov. 1982, pp. 7306–7313.

Uchida et al., "Liquid Crystal Orientation on the Surface of Obliquely-Evaporated Silicon Monoxide With Homeotropic Surface Treatment", Japanese Journal of Applied Physics, vol. 19, No. 11, Nov. 1980, pp. 2127–2136.

Primary Examiner—Stanley D. Miller
Assistant Examiner—Trong Phan
Attorney, Agent, or Firm—Mason, Fenwick & Lawrence

[57] ABSTRACT

Eyewear has variable transparency provided by a lens made of a non-diffusing dichroic liquid crystal cell with nematic-cholesteric phase change. A voltage source supplies an adjustable voltage to the liquid crystal cell; adjustment of the voltage to change the transparency of the lens is effected by a photocell which senses ambient light, or by manual control, or both.

17 Claims, 1 Drawing Sheet

ADJUSTABLE TRANSPARENCY SPECTACLES

This invention concerns adjustable transparency eyewear, such as spectacles and visors. More particularly, the invention concerns spectacles equipped with liquid crystal means allowing the user to adapt the transparency of lenses to variation in external luminosity, even if sudden.

As is well known, whenever the external luminosity is suddenly reduced or increased, conventional sunspectacles now in use have the deficiency of an annoying sensation of darkening or of dazzling, with an objective and sudden lessening of visual capacity, capable of causing substantial risks to the user.

An example of the foregoing is the effect on the driver of a car upon entering or exiting from a road tunnel.

There presently are available some sun spectacles, with lenses in photochromic glass, which effects at least a partial reduction of these difficulties. Actually said type of glass has the property of becoming absorbent, and therefore dark, under the action of light, and clear under conditions of reduced luminosity, thus allowing the production of lenses having the transparency thereof adjustable in an adequate manner, but not with that speed of intervention required and needed in special situations.

Actually the time of variation in the transparency should not exceed 1/10th of a second in order to minimize the referred to phenomena of darkening and of dazzling, while that typical of the photochromic glasses is in the order of several seconds.

Furthermore, with the photochromic glasses, it is impossible to operate directly upon the transparency of the lenses, since the latter depends directly on the quantity of light recently absorbed.

Other means are also known, capable of regulating the transparency of an opening, such as for instance the devices formed by two polarizers of plastic material, placed one upon the other and assembled in such a way as to be able to be relatively rotated, thus allowing adjustment of the transparency within wide limits. However, this apparatus is not suitable to being readily assembled in a pair of spectacles, since in order to effect the mechanical operation above described, there would be required a structure that is not the compact and light weight structure which is typical of spectacles.

The evolution of electronic technology in the field of display devices, used for the presentation of images, has led to the production of electrooptical; cells, as well as of similar contrivances which, in some special embodiments, are capable of rapidly adjusting the transparency thereof.

However, it is to be noted that, for the specific application of these cells to adjustable transparency lenses for spectacles, they should necessarily be able to satisfy the following requirements:
  absence of light diffusion phenomena
  adequate width of the visual angle
  uniformity of light transmission
  sufficient transparency
  no need of polarizers Adjustable transparency spectacles including liquid crystal cells are disclosed in WO 81/02795. In that disclosure, however, the lenses are provided with layers of polarization material.

To provide lenses for adjustable transparency spectacles, having the above referred to characteristics, the present invention uses liquid crystals cells of the dichroic type.

Cells of this glass are capable of causing variation of the transparency without any light diffusion, and without requirement the use of polarizers.

As a general rule, by dichroic cells is meant those in which the liquid crystal has dichroic properties. They mostly are derived from a small percentage of one or more dichroic dyes, whose molecules show an average alignment parallel to that of the liquid crystal holding them in solution.

The fundamental property of a dichroic element (material and/or substance) is that of absorbing light in a greater measure when the electric field of an incident electromagnetic wave (perpendicular to the direction of propagation and being oriented along the plane of polarization) is parallel to a characteristic direction thereof.

By dichroic ratio is meant the ratio between the maximum and minimum optical densities, which can be measured, under polarized light, parallel-wise and perpendicular-wise in reference to the characteristic direction of the dichroic element.

A liquid crystal containing in solution a dichroic dye behaves as a dichroic element, whose characteristic direction can be modified, for instance, under the action of an electrical field.

Several types of dichroic liquid crystal cells are known. The first ones to be studied made use of relatively simple alignments of the liquid crystal, in combination with a polarizer (Guest-Host effect).

Since the latter absorbs—ideally—at least one half of the incident light, it is impossible to obtain a maximum transmission of light.

However, there exist some other types of dichroic cells, known as phase change cholesteric-nematic, or White-Taylor type cells which, thanks to more complex alignments of the liquid crystal, permit the avoidance of the polarizer devices.

In the case of the latter, the possible conditions of the orientation of the cell molecules can be stated as follows (for an exact description there is used, in the following description and claims, the term "horizontal" to indicate a direction parallel to the planes of the walls containing the liquid crystal within the cell, and the term "vertical" to indicate the orthogonal direction).

In a first, extreme condition, in correspondence with the various layers of the liquid crystal, there are obtained different orientations of the molecules in the horizontal plane, or at a small angle thereto, in such a way that all the components of light propagating vertically are absorbed in different layers, according to the plane of polarization.

In a second extreme condition, the orientation of molecules is vertical or nearly so, and the light propagating vertically is not (in ideal operation) absorbed.

Intermediate conditions between these two extreme conditions, corresponding to intermediate angles of molecules with the horizontal plane, permit continuous change in the absorption of light.

Said conditions can practically be obtained in the above referred to White-Taylor type cells, owing to the presence of a liquid crystal having a torsion when it is horizontally aligned. It can be due, in part or totally, to different horizontal directions imposed on the liquid crystal by the two walls of the cell. Besides, a spontaneous torsion, that is in absence of constraints on the walls, being due to the presence of optically asymmetrical molecules, is a well known phenomenon, which is easily verified through the addition of chiral molecules. It characterizes the cholesteric liquid crystals and it can be quantized through the pitch (rightwise or leftwise) of the helicoidal configurations which are obtained. The ratio between the thickness and the pitch supplies the spontaneous torsion (in round angles, i.e. in fractions or multiples of 360 degrees. The nematic liquid crystals can be considered a particular case in which the pitch is infinite.

In the liquid crystals, the index of refraction quite near to 1.5 implies that high angles, with reference to the vertical direction, of the direction of propagation of light in the air, correspond to relatively small angles within the liquid crystal.

There follows from it an operation of the cell even for directions of light different from the vertical, which satisfies one of the essential requirements for implementing the invention.

However, in order that all light be absorbed efficiently by the twisted structure, it is required that the product of the pitch by the optical anisotropy (difference between the extraordinary and the ordinary indexes of refraction) be small in reference to the wave length. In particular, the double refraction of the liquid crystal should be small see the Digest of the 1984 S.I.D. (Society for Informations Displays) Symposium, the contribution 13.3 by J.F. Clerk and al., owing to the fact that the pitch cannot be too small with reference to the thickness of the liquid crystal, since otherwise with the transitions there tend to be formed many disorderly alignments which cause an undesired diffusion of light, so that the liquid crystal appears to darken.

It is also to be taken into account the fact that the contrast to be obtained with the cells depends upon the alignment of the molecules of the dichroic dye, which oscillate continuously around their middle positions, while such phenomenon is expressed through an "order parameter" which can vary between 0 (lack of alignment) and 1 (no oscillations).

The requirement for some high value of the order parameter is the limit for the concentration of the dyes, and therefore for their absorbing power, so that the thickness of the liquid crystal cannot go under a given value, being in practice a thicknesses of 4–14 $\mu$m, with the consequence of unavoidable increases of the pitch's value.

In any case the cells as described by White and Taylor (Journal of Applied Physics, Vol. 45, page 4718 foll., November, 1974) in their generality did not show the specifications required for avoiding the mentioned difficulties of light diffusion, and therefore they cannot be considered as suitable for the objects of this invention.

However, there exist, starting from 1980, some cholesteric-nematic phase change cells that have been shown, according to the present invention, to be capable of varying their transparency without evidencing the phenomenon of light.

Such cells have been obtained through a narrow control of the alignment imposed upon the liquid crystal by the surfaces and by the pitch of the spontaneous torsion of the liquid crystal. Cells of this category are suitable for carrying out the objects of this invention.

A first type of dichroic cells that has been found to be non diffusing does absorb the light at rest (that is in the absence of electrical excitation). In this case use is made of a liquid crystal having a positive dielectric anisotropy, in which the dielectric constant, measured along the orientation's direction of the molecules, is greater than that perpendicularly measured. Under the action of an electrical field the molecules tend to arrange themselves parallel to the former, and therefore vertically (in the presence of flat electrodes on the surfaces).

From a structure of the cholesteric type one therefore passes to another of nematic type, and the cell from being absorbent becomes transparent.

In a first subtype of said cells, which can be employed in this invention, the alignment as imposed on the liquid crystal from one of both walls is parallel or almost parallel to them, according to a prefixed direction.

Among this subtype are preferred the cells of the type in which the said alignment is almost parallel, and more precisely, it is inclined with reference to a horizontal plane, preferably by 2°–15°, and in any case no more than 25°.

Besides, the orientation at rest of the liquid crystal through the thickness of the cell should have an effective total torsion included between about ¼ of a round angle, i.e. 90 degrees and 2 round angles, and preferably between 0.5 and 1.5 round angles.

This is obtained by selecting the pitch in ratio to the thickness of the liquid crystal, and/or actually stressing a fixed total torsion, which can even be more than ¼ round angle more or less than the spontaneous one, through a parallel, or almost parallel, alignment also on the second wall.

In any case the alignment should be prefixed in an uniform way also on the second wall; however there can be accepted all inclinations being included between the vertical and the horizontal.

In a second subtype the alignment as imposed upon the liquid crystal by both walls is almost a vertical one, but the ratio between the thickness and the pitch is little greater (1–2 times) to a critical value being quite near to one (equal to $K_{33}/2K_{22}$). Then the orientation of the liquid crystal in the central parts of the layer is almost horizontal and twisted. However, upon the variation of the electric field, the transparency shows changes in steps, with phenomena of hysteresis. The same renders this second subtype of cells unsuitable for obtaining a gradual adjustment of the transparency.

There does exist a second type of dichroic cells that have been shown non diffusing, which transmit the light at rest while they absorb the same in the excited state, which appear to be completely suitable for use in this invention.

In their case also the alignment as imposed by the walls is almost vertical, but the ratio between thickness and pitch is lower than the aforesaid critical value, and therefore the orientation at rest happens to be almost vertical.

In said cells there is employed a liquid crystal with negative, instead of positive, dielectric anisotropy, the molecules of which tend to place themselves perpendicularly to the electric field. For purposes of this invention, there are to be preferred cells in which the almost vertical alignment on the walls is well controlled, with directions varied by 1–10 degrees from the vertical, preferably 2–5 degrees and preferably according to planes of the walls having angles quite near to the spontaneous, total torsion of the liquid crystal, through a thickness being equal to that of the cell, which in this case is included between ¼ and 1.1 revolutions (Swiss Patent No. 639001, Ebauches S.A., inventor F. Gharadjedaghi).

These latter cells are the most suitable for the adjustable transparency spectacles, in accordance with the present invention, inasmuch they avoid the risk that when the electric excitation is missing, the spectacles might dangerously be darkened. However, even the above referred to cells, non diffusing and absorbing the light at rest, can be employed for the objects of this invention, but by not including the above referred to safety requirement.

Therefore the specific object of this invention is to provide adjustable transparency spectacles including lenses formed by non diffusing liquid crystal cells, means suitable for applying an electric voltage to said cells and means for adjusting said voltage, characterized in that said cells are cholesteric-nematic phase change dichroic liquid crystal cells which transmit the light at rest and absorb the light in their excited state, with a liquid crystal having a double refraction lower than 0.12 and a negative dielectric anisotropy, an alignment vertical or almost so being imposed on the molecules of the crystal by the walls, and the value of the spontaneous pitch being equal to 0.9–4 times the thickness of said cell.

Preferably the pitch is equal to 1.1–1.7 times the said thickness; to said values there corresponds a spontaneous, total torsion of the liquid crystal through the thickness of the cell being included between 6/10 and 9/10 round angle.

Advantageously the said alignment shows a deviation form the vertical equal to 1°–10°, and it preferably takes place along planes mutually forming some angles almost equal to the spontaneous total torsion of the liquid crystal through the thickness of the cell. The value mostly preferred for this deviation is 2°–5°.

Alternatively, as already stated, there can be employed according to this invention also the non diffusing dichroic cells, which absorb the light at rest and transmit the same light in their excited state, with a liquid crystal having a double refraction lower than 0.12 and a positive dielectric anisotropy, an alignment being imposed upon the crystal form at least one of the walls, which alignment is parallel or almost so to the latter, according to a prefixed direction, the value of the pitch being higher than half of the thickness of the cell itself, and the effective torsion, at rest, being equal to ¼-2 round angles, and preferably, to ½-3/2 round angles.

Preferably the said alignment makes with the horizontal an angle not greater than 25°, while in the most preferred embodiment it makes an angle of about 2°–15°.

For instance, the technique which permits imposing on the liquid crystal a prefixed orientation and inclination in correspondence of the walls which it is contact with, are well described (T. Uchida and AA.: "Liquid Crystal Orientation on the Surface of Obliquely Evaporated Silicon Monoxide with Homeotropic Surface Treatment", Japanese Journal of Applied Physics, vol. 19 p. 2127 (1980)).

They typically consist of processes of molecular projection, in vacuo, of a thin layer (5–100 nm) of Si, $ZrO_2$, $CaF_2$ or $MgF_2$, followed by the treatment with a surface-active agent (for instance lecithin or several components within the families of sylans or of the metal-organic complexes) and/or by the unidirectional wiping of the surface with a soft cloth, possibly impregnated with very thin particles of abrasive, under controlled conditions of pressure and duration.

The technique of production and the theory of operation of the cells transparent at rest, are described by F. Gharadjedaghi in "A Positive Contrast Guest-Host Display Using a Liquid Crystal of Negative Dielectric Anisotropy", Molecular Crystal and Liquid Crystals, vol. 68, pag. 126 foll. (1981) and by F. Gharadjedaghi and R. Voumard, in "Mathematical Simulation of a Positive Contrast Guest-Host Display Using Nematic Cholesteric Phase-Change", Journal of Applied Physics, vol. 53, pag. 7306 foll. (1982).

The absorbing at rest cells, employed in this invention, are described, for instance, by K. Suzuki et al in "A Multiplexed Phase-Change Color LCD", Trans. on Electronic Devices, Vol. 28 pag. 719 foll. (1981), by K. Suzuki and S. Hasegawa in "Design Considerations for Phase Change Type Guest-Host Colour LCD", Proceedings of the first European Display Research Conference, Munich, September 81, pag. 72 foll. (as published by S.I.D.), and by F. Gharadjedaghi and E. Saurer in: "A novel type of invented dichroic Display Employing a Positive Dielectric Anisotropy L.C.", IEEE Trans. on Electronic Devices, vol. 27, page 2063 foll. (1980).

Suitable mixtures of a dye and combinations of a dye with liquid crystals, are described, for instance, in the contribution 13.2 by U. Classen, et al. (Bayer, Leverkusen) of the 1984 S.I.D. Symposium (on pag. 209 of the Digest), as well as in the article by B. Scheuble et al. (Merck's, Darmstadt) "New Black L.C. Guest-Host Systems for Indoor and Outdoor Applications", S.I.D. Proceedings, vol. 25, pag. 25 (1984).

The processes also for deposition of the required layers of transparent conductor are well known in the art, as well as is the possibility of providing the cells between supports of plastic material (polyester resins) (H. Inone and A. Kikuyama; "Homogenous Molecular Alignment Technique for Polymer Film LCD", Proceedings of the First European Research conference, pag. 28 (Munich 1981), and P.A. Penz, J.B. Sampsell and D.R. Collins, "A Plastic LCD Design with High Reliability and Color-Free Readability", IEEE Trans. on Electronic Devices, vol. 22 (1985), pag. 2206).

It is well known that in order to obtain uniform transparencies also at intermediate levels, the dichroic cells, we have dealt with, require a very high precision (better than +/− 10%) in the control of interspace thickness, upon the variation of which there also changes the applied voltage to transparency relationship.

For that purpose, the known technologies propose to interpose between the internal walls a plurality of spacers, for instance some microscopic lengths of glass fibers, and to ensure some pressure on the spacers by the walls. This can be obtained through the sealing of the inside interspace, under conditions of some small negative pressure as compared to atmospheric pressure, and/or by coupling surfaces whose camber is slightly different, which result, after some gluing in correspondence of their edges, pressed one against the other, owing to internal stresses (U.S. Pat. No. 4,150,878, Barzilai et al.). It is anyway required that the start surfaces have differences of depth and camber, with reference to the ideal one, contained respectively within a few micrometers and within a few micrometers/sq. cm.

The standard technique of the liquid crystal cells provides the use of glass flat supports, obtained by the float process, that causes the plates to solidify as they float on molten metal. However there is no knowledge of descriptions relating to liquid crystal cells with curved rigid supports, certainly more suitable for the protective glasses according to this invention, since they permit the reduction of any undesired effect of astigmatism (as well as of dispersion of colours) in the side vision (Tscherning's diagram).

As already known, the normal absorbent lenses are obtained through processes of blowing and casting of either glass or organic glass. The higher quality and cost lenses are obtained by working the glass through grinding processes in contact with metallic "coats", followed by polishing, using the same technique suitable for graduated lenses and obtaining the same limits for the results.

Said limits are (as a total) currently considered as equal to $+/- \frac{1}{8}$ diopter: f.i. refer to V. Ronchi, "Lenses for spectacles', Zanichelli, 1962. Said limits however are utterly unsuitable for producing the curved lenses capable of meeting the aims of this invention. On the other side, it is well known that the processes of optical manufacture, that is those of grinding and polishing, under conditions of closer control, permit the attainment of a degree of precision within tenths of a micrometer, as needed by precision optics and more than suitable for dichroic cells.

For the implementation of the adjustable transparency spectacles, it is therefore proposed to employ the lenses processed, at least on their inner side, with the improved technologies above referred to, with such a precision as not to give way to a difference of dimension and of camber, with respect to the ideal surface, respectively limited within a few micrometers and within a few micrometers/sq. cm.

Said lenses may be made out of glass or of a plastic material, and they will be preferably treated or coloured in such a way as to absorb the ultraviolet rays as well as to protect the dichroic dyes form losing colour.

Further, in spectacles according to this invention, the above referred to means for applying the electric voltage are formed by an electronic circuit which generates, at the terminals of the cell, an adjustable voltage, whose effective value is higher than the threshold voltage, does not contain any direct current components and has a frequency sufficiently high as not to allow the passage of ions into the liquid crystal.

Preferably, the said electronic circuit includes, an inductor, electrically resonant with the cells' capacitances.

The voltage being generated by the electronic circuit is adjusted by manual and/or automatic means. The latter may be formed, in particular, by electronic circuits actuated by a photocell.

The manual means can, on the contrary, be formed by electronic circuits controlled by lightly touched keys, or by a potentiometer, by a variable capacitor or by a variable inductor, or by any combination of them.

Also, as far as their shape is concerned, spectacles according to this invention can be implemented, instead of having two separate lenses, with just one continuous element, of plastic material, which is shaped as a visor.

BRIEF DESCRIPTION OF THE DRAWINGS

In FIG. 1 there is shown in cross-section a liquid crystals cell 1 making up one lens, and comprising spaced supports 2 of glass or of a plastic material, with sealant 3 of resin or frit for the interspace 4, which is filled with liquid crystal and which is therefore suitable for making a dichroic cell.

Figure 1:
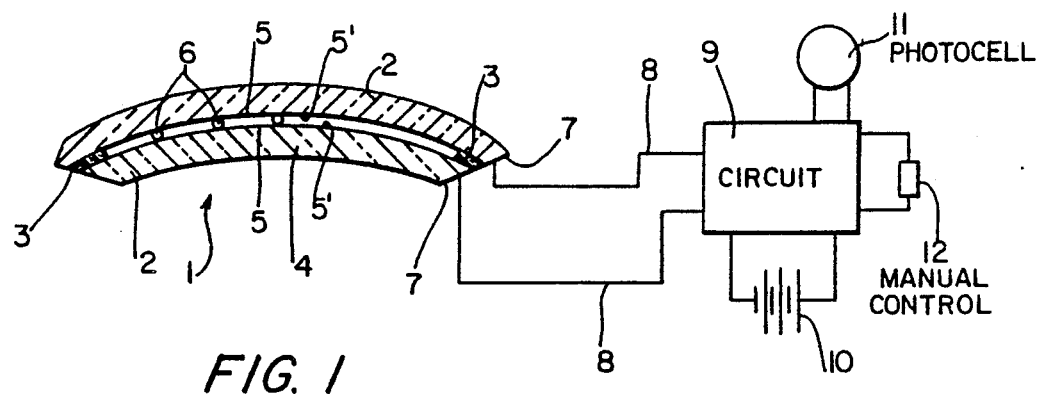
FIG. 1 shows in cross-section a lens and related circuit of spectacles according to the invention.

Upon such of the facing surfaces of supports 5, there is placed a transparent conducting layer 5', as well as layers required for the alignment of the liquid crystal, while between said surfaces, spacers 6 are deployed.

The peripheral sealant 3 has a small opening (not shown) for the negative pressure filling of the interspace 4 with the liquid crystal, to be thereafter sealed. The opening can be replaced by a hole in any of the supports 2.

Contacts 7 to the conductive layer 5' are connected by wires 8 to an electronic circuit 9, which supplies electric voltage to the cell 1. Said circuit 9 generates, at the contacts 7 an adjustable voltage, whose effective value is higher than the threshold voltage, does not contain any direct current components and has a frequency sufficiently high as not to allow the passage of ions into the liquid crystal.

A power source 10 for the circuit 9 is in the form of a battery, but could be eliminated if photocell 11, connected to circuit 9, generates enough power. The photocell 11 and manual control 12 for adjusting the voltage, which can be for instance an electronic circuit, controlled by lightly touched keys, allow, together or alternatively, the adjustment of the voltage generated by the circuit, as well as the control of the lens' transparency.

The lens and other components shown in FIG. 1 are supported by a suitable frame for eyewear, such as spectacles, which can house the miniaturized circuit, or, alternatively, the circuit can be contained in a small box hanging from earpieces by a string.

The invention will now be described, in an illustrative way, by the following examples concerning some of its specific embodiments.

EXAMPLE 1

Transparent lenses optionally corrective, made of glass or of the organic material known as CR39, dyed while in molten condition, in such a way as to absorb ultraviolet rays, whose thickness in about 0.7 mm, in the case of glass, and about 1 mm, in the case of plastic, are worked in pairs, with a difference in camber equal to about 2 um/sq. cm, according to the U.S. Pat. No. 4,150,878 of Barzilai, Maltese and Ottavi, the faces of which are to enclose liquid crystal, and they are then cut out according to the shape of the frame.

The internal surfaces are activated by "plasma etching" and treated with "magnetron sputtering", by firstly depositing a blocking layer of 0.1 $\mu$m of $Al_2O_3$, and then a second layer, of about 0.1 $\mu$m in thickness of indium and tin oxide (ITO), having a surface resistivity of about 100 ohm/sq. cm and a transparency better than 85%. The treatment is also performed on the edges, where successively some gold is evaporated, in order to obtain some contact areas. By reduced pressure thermal evaporation of 0.04 $\mu$m of SiO, at a grazing angle equal to approximately 60° from the normal, followed by a rubbing with abrasive, one can obtain surfaces which will allow an almost horizontal orientation of the liquid crystal, with an inclination equal to 3° with reference to the walls. On the edge of the convex face, there is also deposited, by silk screen printing, a peripheral ring of epossidic resin, non polymerized (Allestik No. 517), with an interruption through which the liquid crystal will be caused to enter. Minute lengths of glass fibers, whose diameter is 8 um, are scattered upon the convex surface and the concave surface is then pressed upon the convex surface. This operation is performed by sealing in vacuum a packet of thermoplastic material containing the lens. There follows the baking of the resin at 80° C. for 5 hours. The internal surfaces are compressed through the spacers and there is obtained the required uniformity of thickness for the space 4. The liquid crystal is then caused to the space 4, which is under vacuum.

This process is performed at about 80° C. and inside a vacuum chamber, by plunging for a sufficient time (some minutes) into the liquid crystal the edge of the lens in correspondence with the discontinuity of the glueing. Said discontinuity is then sealed with resin sealant.

Figure 2:
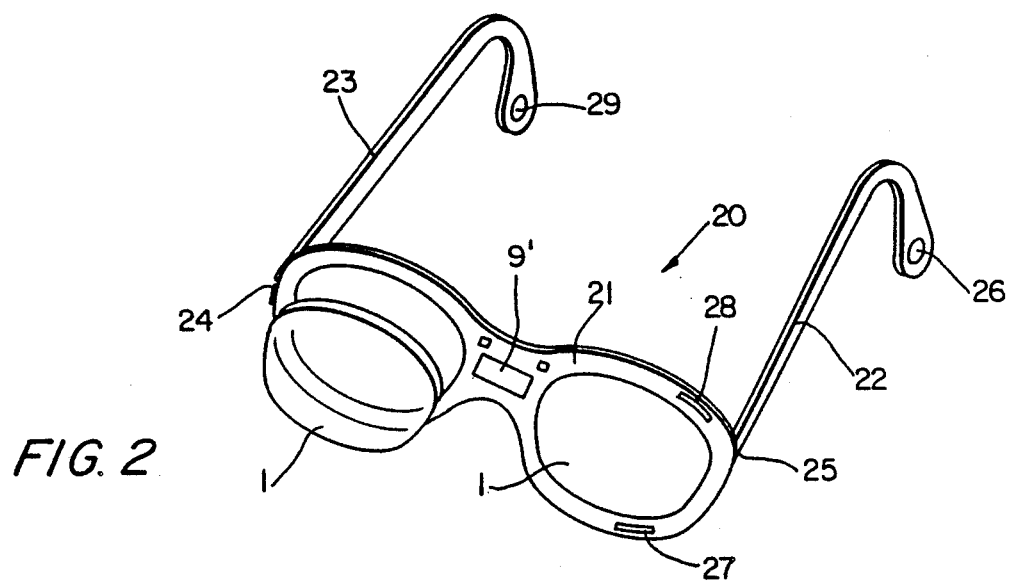
FIG. 2 is a perspective view of eyewear employing the lens and components as in FIG. 1.

There is employed a liquid crystal having positive dielectric anisotropy $\Delta\epsilon=5$ and low double refraction ($\Delta n=0.08$), which also has dichroic dye and chiral additive. The structure of the eyewear is completely optional. As shown in FIG. 2, the eyewear is a spectacles 20 comprised of frame 21 and earpieces 22 and 23, hinged through special platinum plated metallic hinges 24 and 25, providing several separated electric confections (not shown). Hinge 25 is constructed with a switch, so as to break a circuit to battery 26 in earpieces 22 whenever it is folded in. The frame 21 comprises a core (one millimeter thick) of resin loaded with carbonium fiber, and is laminated with layers of copper connected to hinge 25, and said parts are embedded in the resin. The lenses 1 are pressure moulded into the frame 21 which, for this purpose, has its lower part made with thermoplastic resin only. The construction of the earpieces permits their hot bending for better fit to any user.

The spectacles 20 weigh about 55 g., are normally dark, having a transparency around 15-25%, for light rays orthogonal to, or at 45° with the surface. Said values can be adjusted up to maximum transparencies, equal to respectively 70-60% when maximum voltage is applied to the lenses.

The integrated circuit 9' automatically controls the transparency of the lenses 1; furthermore the user is able, by pressing on the two keys 27, 28, to brighten or darken them. The lenses 1 can operate between 5° and 40° C., with the liquid crystal operable, and the duration of the battery is equal to a least 200 hours, depending upon the conditions of use.

EXAMPLE 2

The spectacles 20 may be manufactured using the technology of printed circuits.

On a printed circuit core, there are soldered the electronic components and the spring contacts for the lenses. On frame 21, between lenses 1, there is provided the monolithic integrated circuit 9' which includes a photocell, and other components. Through a process of hot moulding there are applied two external layers of thermoplastic resin. The earpieces 22 and 23 are manufactured of thermoplastic resin with the recesses for lithium battery 26 and for ferrite microtransformer 29. The transformer 29 has the function of minimizing the electrical consumption and enables the use of battery 26 having its voltage lower than the threshold one of the liquid crystal.

There has been employed a microtransformer 29 of special make, whose dispersed inductance resonates with the capacitance of the liquid crystal cells, at the piloting frequency.

The control of the amplitude of the voltage on the secondary of microtransformer 29 is obtained by varying the duration of the pulses applied to the primary.

Each connection spring is manufactured of just one piece of steel, and with electrical contact material suitable for lenses of the corrective type. There may be used various aligning layers, and a different liquid crystal. In this case the grazing evaporation is performed at 80 Degr. C. with $CaF_2$ and it is followed by a surface treatment by immersion in a diluted DMOAP solution (N,N-dimethyl-N-octadecyl-3-aminopropyltrimethox-ylil chloride).

For the liquid crystal, there is employed a mixture having low double refraction ($\Delta n=0.08$) and negative dielectric anisotropy ($\Delta\epsilon-1.5$), plus a chiral additive and some dichroic dye.

The integrated photodiode is differently connected to the remainder of the circuit 9', in such a way as to invert its action. There is thereby obtained a pair of spectacles normally clear (80-70%), being capable of darkening up to 30-40% (for the orthogonal direction and for that inclined by 45 deg. C., respectively). The endurance of the battery depends upon the conditions of use and appears to be 400 hours at least.

Figure 3:
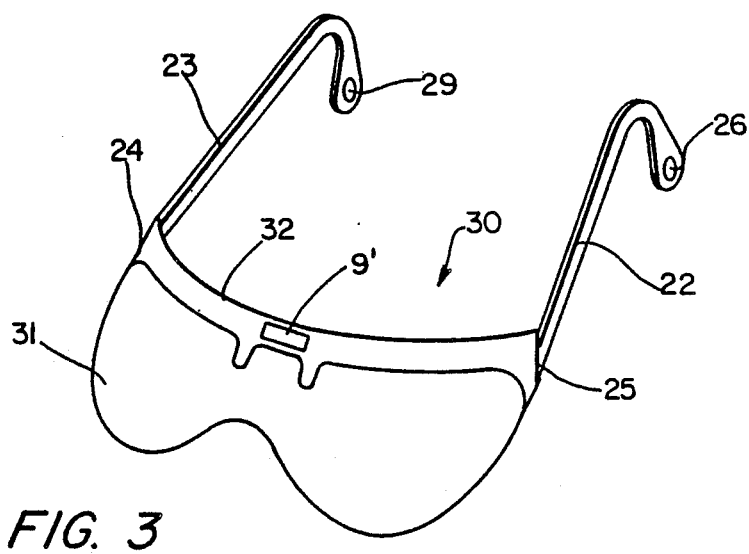
FIG. 3 is a perspective view of an alternate embodiment.

Another construction of the invention, shown in FIG. 3, uses laminated sheets, made of transparent and flexible plastic material, for containing the liquid crystal. There is shown a visor-like eyewear 30, in which there is a continuous lens extending in front of both eyes of the wearer. The lens 31 is constructed by a lamination process, in which some layers of polyester resin (Mylar) are assembled together with a liquid crystal and an epossidic adhesive. There is employed a continuous manufacturing process, starting from ribbons of sheeted mylar. 0.5 mm, thick, which are made to pass through vacuum chambers and machines in which they undergo the same treatments which have been already described. In this case, the uniformity of the thickness for the inner space is guaranteed by the residual internal depression after the filling with liquid crystal and the polymerization of the epossidic resin. The latter takes place in a mold, in which the surfaces are glued to their final curved shape after having been cut from the ribbon in the required shapes. The conductive paths are embedded into the lamination and there is obtained a lens 31, cylindrically bent. The lens 31 is glued to a frame 32 carrying the circuit 9', the hinges 24 and 25 connecting circuit 9' to the earpieces 22 and 23. Eyewear 30 is a rather lighter structure (40 gr.), which is also more economical when produced on a sufficiently large scale.

I claim:

1. Eyewear having adjustable transparency comprising:

at least one lens comprising means for varying the transparency thereof in response to a variation of voltage applied thereto, means for supplying said variable voltage connected to said transparency varying means, means for varying said variable voltage from said voltage supplying means applied to said transparency varying means, said means for varying the transparency of said lens comprising a liquid crystal cell including a pair of spaced transparent supports each having a transparent electrode to which said variable voltage from said voltage supplying means is applied to produce an electric field having a variable strength, a cholesteric-nematic phase change dichroic liquid crystal between said supports which transmits light in the absence of said electric field and which absorbs light in relation to the strength of said electric field, said liquid crystal having a double refraction lower than 0.12 and a negative dielectric anisotropy, at least one of said cell supports including means for imposing on the molecules of said liquid crystal a substantially vertical alignment, said liquid crystal having a spontaneous pitch value which is equal to 0.9–4 times the thickness of said cell.

2. Eyewear according to claim 1, wherein said spontaneous pitch value is equal to 1.1–1.7 times the thickness of the cell.

3. Eyewear according to claim 2, wherein said liquid crystal has a spontaneous total torsion between 6/10 and 9/10 of a round angle.

4. Eyewear according to claim 1, wherein said liquid crystal has a deviation from the vertical of said alignment between 1°–10°.

5. Eyewear according to claim 1, wherein said liquid crystal has a deviation from the vertical of said alignment between 2°–5°.

6. Eyewear according to claim 1, wherein said liquid crystal has a spontaneous total torsion and said alignment forms angles which are substantially equal to the spontaneous total torsion of the liquid crystal through the thickness of said cell.

7. Eyewear apparatus having adjustable transparency comprising:
   at least one lens comprising means for varying the transparency thereof in response to a variation of voltage applied thereto,
   means for supplying said variable voltage connected to said transparency varying means,
   means for varying said variable voltage from said voltage supplying means applied to said transparency varying means,
   said means for varying the transparency of said lens comprising a liquid crystal cell including a pair of spaced transparent supports each having a transparent electrode to which voltage from said voltage supplying means is applied to produce an electric field having a variable strength, a cholesteric-nematic phase change dichroic liquid crystal between said supports which absorbs light in the absence of the electric field and which transmits light in relation to the strength of said electric filed, said liquid crystal having a double refraction lower than 0.12 and a positive dielectric anisotropy, at least one of said cell supports including means for imposing on molecules of said liquid crystal an alignment substantially parallel thereto, said liquid crystal having a spontaneous pitch value which is more than one-half the thickness of said cell, and an effective torsion, at rest, which is substantially equal to ¼–2 round angles.

8. Eyewear according to claim 7, wherein the effective total torsion, at rest, of said liquid crystal through the thickness of said cell is between ¼ and 3/2 round angles.

9. Eyewear according to claim 7, wherein said alignment has an angle relative to horizontal not greater than 25°.

10. Eyewear according to claim 7, wherein said alignment has an angle relative to horizontal between 2°–15°.

11. Eyewear according to claim 1 or claim 7, wherein said voltage supplying means comprises means for supplying voltage having an effective value higher than a threshold voltage, which does not contain any direct current components, and which has a frequency sufficiently high to prevent a passage of ions into said liquid crystal.

12. Eyewear according to claim 1 or claim 7, wherein said voltage varying means comprises a manually operated control.

13. Eyewear according to claim 1 or claim 7, wherein said voltage varying means comprises means sensitive to an intensity of ambient light.

14. Eyewear according to claim 1 or claim 7, wherein said support comprises means for absorbing ultraviolet rays.

15. Eyewear according to claim 1 or claim 7, wherein said supports of said cell are curved lenses.

16. Eyewear according to claim 1 or claim 7, wherein said lens comprises a continuous element of visor shape extending across eyes of a user.

17. Eyewear according to claim 1 or claim 7, wherein said lens extends in front of only a first eye of a user, and a substantially identical lens extends in front of only a second eye of the user.

* * * * *